(12) United States Patent
Murphy (10) Patent No.: US 11,045,329 B1
(45) Date of Patent: *Jun. 29, 2021

(54) ACETABULAR TEMPLATE COMPONENT AND METHOD OF USING SAME DURING HIP ARTHROSPLASTY

(71) Applicant: Stephen B. Murphy, Winchester, MA (US)

(72) Inventor: Stephen B. Murphy, Winchester, MA (US)

( * ) Notice: Subject to any disclaimer, the term of this patent is extended or adjusted under 35 U.S.C. 154(b) by 116 days.

This patent is subject to a terminal disclaimer.

(21) Appl. No.: 16/284,441

(22) Filed: Feb. 25, 2019

Related U.S. Application Data

(63) Continuation of application No. 15/887,604, filed on Feb. 2, 2018, now Pat. No. 10,251,760, which is a
(Continued)

(51) Int. Cl.
*A61F 2/46* (2006.01)
*A61B 17/17* (2006.01)
(Continued)

(52) U.S. Cl.
CPC ........ *A61F 2/4609* (2013.01); *A61B 17/1746* (2013.01); *A61F 2/30942* (2013.01); *A61F 2/34* (2013.01)

(58) Field of Classification Search
CPC .. A61F 2/46; A61F 2/4609; A61F 2/34; A61F 2/30; A61F 2/30942; A61B 17/58; A61B 17/17; A61B 17/1746
See application file for complete search history.

(56) References Cited

U.S. PATENT DOCUMENTS

| 3,457,651 A | 7/1969 | Kaeck |
| 5,056,523 A | 10/1991 | Hotchkiss, Jr. et al. |

(Continued)

FOREIGN PATENT DOCUMENTS

| DE | 19521060 A1 | 12/1996 |
| DE | 102004010332 B3 | 10/2005 |

(Continued)

OTHER PUBLICATIONS

Archbold, H. A.P., et al., "The Transverse Acetabular Ligament: An Aid to Orientation of the Acetabular Component During Primary Total Hip Replacement," The Journal or Bone & Joint Surgery (Br), vol. 88, No. 7, Jul. 2006, pp. 883-886.
(Continued)

*Primary Examiner* — Christopher J Beccia
(74) *Attorney, Agent, or Firm* — Cesari and McKenna, LLP; Michael R. Reinemann (57) ABSTRACT

A medical imaging device takes one or more images of the local anatomy of a patient undergoing a surgical procedure. A surface model generator receives the one or more images and generates a 3-D surface model of the patient's anatomy. A fabrication device utilizes the 3-D surface model to fabricate a template custom designed to match the surface of the patient's anatomy. Attached to the template is a directional guide vane. The fabrication device is configured to create a template and directional guide vane such that, when the template is fitted to the patient's anatomy, the directional guide vane points along a predefined orientation relative to the patient's anatomy. A physician uses the directional guide vane as a visual guide or cue for installing an implantable prosthetic component during a surgical procedure.

15 Claims, 11 Drawing Sheets

Related U.S. Application Data continuation of application No. 14/661,607, filed on Mar. 18, 2015, now Pat. No. 9,883,954, which is a continuation of application No. 12/263,808, filed on Nov. 3, 2008, now Pat. No. 8,986,309.

(60) Provisional application No. 60/984,541, filed on Nov. 1, 2007.

(51) Int. Cl.
*A61F 2/30* (2006.01)
*A61F 2/34* (2006.01)

(56) References Cited

U.S. PATENT DOCUMENTS

| | | |
|---|---|---|
| 5,086,401 A | 2/1992 | Glassman et al. |
| 5,122,145 A | 6/1992 | Fishbane |
| 5,127,920 A | 7/1992 | MacArthur |
| 5,141,512 A | 8/1992 | Farmer et al. |
| 5,141,513 A | 8/1992 | Fortune et al. |
| 5,320,625 A | 6/1994 | Bertin |
| 5,327,907 A | 7/1994 | Fischer |
| 5,376,093 A | 12/1994 | Newman |
| 5,515,616 A | 5/1996 | Merkin |
| 5,571,111 A | 11/1996 | Aboczky |
| 5,697,939 A | 12/1997 | Kubota et al. |
| 5,776,143 A | 7/1998 | Adams |
| 5,824,007 A | 10/1998 | Faraz et al. |
| 5,916,219 A | 6/1999 | Matsuno et al. |
| 6,090,114 A | 7/2000 | Matsuno et al. |
| 6,132,437 A | 10/2000 | Omurtag et al. |
| 6,228,089 B1 | 5/2001 | Wahrburg |
| 6,273,891 B1* | 8/2001 | Masini .............. A61F 2/30724 606/91 |
| 6,290,196 B1 | 9/2001 | Mayenberger |
| 6,314,312 B1 | 11/2001 | Wessels et al. |
| 6,395,005 B1 | 5/2002 | Lovell |
| 6,482,237 B2 | 11/2002 | Mosseri |
| 6,634,883 B2 | 10/2003 | Ranalli |
| 6,743,235 B2 | 6/2004 | Subba Rao |
| 7,090,677 B2 | 8/2006 | Fallin et al. |
| 7,182,766 B1 | 2/2007 | Mogul |
| 7,201,756 B2 | 4/2007 | Ross et al. |
| 7,344,542 B2 | 3/2008 | Coliazo et al. |
| 7,419,492 B2 | 9/2008 | Yoon et al. |
| 7,651,501 B2 | 1/2010 | Penenberg et al. |
| 7,780,672 B2 | 8/2010 | Metzger et al. |
| 8,267,938 B2 | 9/2012 | Murphy |
| 8,986,309 B1 | 3/2015 | Murphy |
| 9,101,378 B2 | 8/2015 | Murphy |
| 9,474,470 B2 | 10/2016 | Murphy |
| 9,883,954 B1* | 2/2018 | Murphy .............. A61F 2/4609 |
| 10,004,752 B2 | 6/2018 | Murphy |
| 10,251,760 B1* | 4/2019 | Murphy .............. A61B 17/1746 |
| 2003/0153829 A1 | 8/2003 | Sarin et al. |
| 2004/0092944 A1 | 5/2004 | Penenberg |
| 2004/0152970 A1 | 8/2004 | Hunter et al. |
| 2004/0210233 A1 | 10/2004 | Yoon et al. |
| 2004/0254586 A1 | 12/2004 | Sarin et al. |
| 2004/0260312 A1 | 12/2004 | Magnusson et al. |
| 2005/0076441 A1 | 4/2005 | Dominati et al. |
| 2005/0107799 A1 | 5/2005 | Graf et al. |
| 2005/0148843 A1* | 7/2005 | Roose ................ A61B 17/17 600/407 |
| 2005/0149050 A1 | 7/2005 | Stifter et al. |
| 2005/0234332 A1 | 10/2005 | Murphy |
| 2006/0025778 A1 | 2/2006 | Ferree |
| 2006/0052795 A1 | 3/2006 | White |
| 2006/0100504 A1 | 5/2006 | Jansen et al. |
| 2006/0161167 A1* | 7/2006 | Myers ............... A61B 17/1746 606/91 |
| 2006/0184177 A1 | 8/2006 | Echeverri |
| 2006/0225529 A1 | 10/2006 | Fischer et al. |
| 2006/0241441 A1 | 10/2006 | Chinn |
| 2008/0255584 A1* | 10/2008 | Beverland ............. A61F 2/4657 606/130 |
| 2008/0287954 A1 | 11/2008 | Kunz et al. |
| 2009/0163922 A1 | 6/2009 | Meridew et al. |
| 2009/0171370 A1 | 7/2009 | Yoon et al. |
| 2009/0254093 A1 | 10/2009 | White et al. |
| 2009/0306679 A1 | 12/2009 | Murphy |
| 2011/0196433 A1 | 8/2011 | Kleiner |
| 2012/0245647 A1 | 9/2012 | Kunz et al. |
| 2013/0006255 A1 | 1/2013 | Murphy |
| 2013/0018430 A1 | 1/2013 | Murphy |
| 2015/0289891 A1 | 10/2015 | Murphy |
| 2017/0035580 A1 | 2/2017 | Murphy |

FOREIGN PATENT DOCUMENTS

| | | |
|---|---|---|
| JP | 2004-89653 A | 3/2004 |
| JP | 2005-111257 A | 4/2005 |
| JP | 2006-501972 A | 1/2006 |
| JP | 2011-502626 A | 1/2011 |
| SU | 441933 A1 | 9/1974 |
| WO | WO-2000/30557 A1 | 6/2000 |
| WO | WO-2001/34017 A2 | 5/2001 |
| WO | WO-2003/009768 A1 | 2/2003 |
| WO | WO-2004/021898 A1 | 3/2004 |
| WO | WO-2005/046451 A2 | 5/2005 |
| WO | WO-2006/109983 A1 | 10/2006 |
| WO | WO-2008/145287 A1 | 12/2008 |

OTHER PUBLICATIONS

Chen, Bin, et al., "Personalized Image-Based Templates for Precise Acetabular Prosthesis Placement in Total Hip Arthroplasty: A Pilot Study," Journal of Zhejiang University—Science B (Biomedicine & Biotechnology), Sep. 11, 2010, pp. 673-680.

Chow, JC, et al., "Evaluation of Intraoperative Pelvic Positioning Using Software-based Computed Tomography/Radiography Matching," International Society for Computer Assisted Orthopedic Surgery, Jun. 2008, pp. 192-194.

English Description of Japanese Publication No. JP2004-089,653, retrieved on Aug. 27, 2014, pp. 1-30.

English Description of Japanese Publication No. JP 2005-111,257, retrieved on Aug. 27, 2014, pp. 1-26.

English Translation of Office Action, from Japanese Patent Office for Japanese Patent Application No. JP 2013-112536, dated Apr. 1, 2014, pp. 1-2.

European Search Report, European Application No. 13153277.2-1659 / 2626032, Applicant: Stephen B. Murphy, dated Mar. 20, 2014, pp. 1-6.

European Search Report, European Application No. 13153236.8-1659 / 2626031, Applicant: Stephen B. Murphy, dated Aug. 22, 2014, pp. 1-5.

Klingenstein, G., et al., "Pelvic Tilt Before and After Total Hip Arthroplasty," International Society for Computer Assisted Orthopedic Surgery, Jun. 2008, pp. 99-100.

Murphy, Stephen, et al., "Evaluation of Intraoperative Pelvic Position During Hip Arthroplasty Using Computed Tomography/ Radiography Matching," Oral Session 18, The 21st Annual Congress of the International Society for Technology in Arthroplasty, Seoul Korea, Oct. 1-4, 2008, one page.

Notification of Transmittal of the International Search Report and the Written Opinion of the International Searching Authority, or the Declaration, International Filing Date: Oct. 30, 2008, International Application No. PCT/US2008/012300, Applicant: Stephen B. Murphy, dated Mar. 5, 2009, pp. 1-8.

U.S. Appl. No. 12/263,808, filed Nov. 3, 2008 by Stephen B. Murphy, M.D. for an Acetabular Template Component and Method of Using Same During Hip Arthrosplasty, pp. 1-29.

U.S. Appl. No. 13/764,637, filed Feb. 11, 2013 by Stephen B. Murphy, M.D. for an Surgical System Using a Registration Device, pp. 1-39.

U.S. Appl. No. 14/661,607, filed Mar. 18, 2015 by Stephen B. Murphy, M.D. for an Acetabular Template Component and Method of Using Same During Hip Arthrosplasty, pp. 1-31.

(56) References Cited

OTHER PUBLICATIONS

U.S. Appl. No. 15/887,604, filed Feb. 2, 2018 by Stephen B. Murphy for an Acetabular Template Component and Method of Using Same During Hip Arthrosplasty, pp. 1.

* cited by examiner

ACETABULAR TEMPLATE COMPONENT AND METHOD OF USING SAME DURING HIP ARTHROPLASTY

CROSS-REFERENCE TO RELATED APPLICATIONS

This application is a continuation of application Ser. No. 15/887,604, filed Feb. 2, 2018, which is a continuation of application Ser. No. 14/661,607, filed Mar. 18, 2015, now U.S. Pat. No. 9,883,954, which is a continuation of application Ser. No. 12/263,808, filed Nov. 3, 2008, now U.S. Pat. No. 8,986,309, which claims priority to U.S. Provisional Patent Application Ser. No. 60/984,541, filed Nov. 1, 2007, which applications are hereby incorporated by reference in their entireties.

The present application also is related to:

U.S. patent application Ser. No. 12/134,545, filed on Jun. 6, 2008 by Stephen B. Murphy for a METHOD AND APPARATUS FOR DETERMINING ACETABULAR COMPONENT POSITIONING, now U.S. Pat. No. 8,267,938, pending application is hereby incorporated by reference in its entirety.

BACKGROUND OF THE INVENTION

Field of the Invention

The present invention relates to medical devices and, more particularly, to devices and methods for determining proper position of implantable surgical components.

Background Information

During hip arthroplasty, a prosthetic component is placed in the patient's acetabulum to receive a prosthetic femur head. Malpositioning of the acetabular component during hip arthroplasty can lead to dislocation, impingement, wear, and may require additional surgeries to correct these problems. Proper positioning of the acetabular component during hip arthroplasty requires that the surgeon know the position of the patient's pelvis during surgery so that the component can be inserted in a proper position relative to the pelvis. Unfortunately, the position of the patient's pelvis varies widely during surgery and from patient to patient. As a result, large errors in component positioning occur if the surgeon assumes that the patient's pelvis is positioned squarely with the operating table, whether in the lateral or supine position. For example, one study showed that patients' pelvises were malpositioned through a range of 33 degrees around the medial-lateral axis, 47 degrees around the longitudinal axis, and 17 degrees around the anterior-posterior axis. (Chow J C, Eckman K, Jaramaz B, Murphy S, Evaluation of Intraoperative pelvic position during hip arthroplasty using computer tomography/radiography matching, International Society for Computer Assisted Orthopedic Surgery, 2008.)

To reduce the likelihood of component malpositioning, the position of the pelvis can be tracked using computer-assisted surgical navigation techniques, but the majority of surgeons do not employ these techniques. More basic surgical technique involves qualitative assessment of the position of the acetabular component compared to the local surrounding bony and soft tissue anatomy that is visible through the incision. One such technique, for example, uses the transverse acetabular ligament as a qualitative marker of orientation of the native acetabulum. (Archbold H A, Mockford B, Molloy D, McConway J, Ogonda L, Beverland D, The Transverse acetabular ligament: an aid to orientation of the acetabular component during primary total hip replacement: a preliminary study of 1000 cases investigating post-operative stability, J Bone Joint Surg BR. 2006 July; 88(7): 883-6.)

Unfortunately, such techniques have limited accuracy for several reasons. First, the transverse acetabular ligament is very close to the center of the acetabulum, and thus geometrically small errors in interpretation of its position can lead to large angular errors in orientation of the acetabular component. Second, since the transverse acetabular ligament defines a line, which is a two dimensional geometric element: it does not provide true three dimensional guidance. Third, since most hips that are worn are also malformed, taking clues from the local malformed anatomy is a fundamentally flawed concept. Further, even if the local anatomy were not abnormal, as may be the case in patients with femoral head osteonecrosis, it is often the case that the native acetabulum is orientated in a much more vertical position than is appropriate for a prosthetic acetabulum. As a result, while the normally formed native acetabulum may provide clues as to where to position the prosthetic acetabulum component, the prosthetic acetabulum component often should not be placed in the same orientation as the normal native acetabulum.

SUMMARY OF THE INVENTION

Briefly, the present invention is directed to a method and device for positioning a surgical implant component. In an embodiment, a medical imaging device is used to take one or more images of the local anatomy of a patient undergoing a surgical procedure. A surface model generator receives the one or more images and uses the information from the one or more images to generate a 3-D surface model of the patient's anatomy. A fabrication device utilizes the information from the 3-D surface model to build a template that is custom designed to match the surface of the patient's anatomy. In the illustrative embodiment, the template is designed so that it will only fit to the patient's anatomy in a single orientation. In particular, the template includes a surface that is shaped to match the surface of the patient's anatomy in a single orientation. The template includes a surgical guide that, in the preferred embodiment, extends from the template. The fabrication device is configured to create a template and surgical guide such that, when the template is fitted to the patient's anatomy, the surgical guide is in a predefined orientation relative to the patient's anatomy. The predefined orientation of the surgical guide is selected by the physician to achieve a desired placement or orientation of an implantable prosthetic component.

During surgery the portion of the patient's anatomy for which the custom template was fabricated is exposed. The custom template is fitted to the patient's anatomy in the single orientation for which it was designed. The template may be secured in place by screws or other fasteners. With the template attached to the patient's anatomy, the surgical guide is disposed in space in a fixed orientation relative to the patient's anatomy, as selected by the physician. The physician then utilizes the surgical guide as a visual positioning guide or cue when installing or attaching a surgical component to the patient in a desired orientation. After the surgical component has been properly attached to the patient, the template may be removed.

In an embodiment, the template and surgical guide are a single piece. In another embodiment, the surgical guide is removably attached to the template. In this embodiment, the surgical guide may be re-used with templates designed for other patients. The surgical guide, moreover, may have a fixed orientation relative to the template, or it may be adjustable in one or more planes or directions. In another embodiment, instead of a surgical guide, a drill guide is attached to the template. The drill guide is used to drill a pilot hole in the pelvis into which a surgical guide may be placed. In this embodiment, once the surgical guide has been installed in the pilot hole, the template and the drill guide may be removed.

BRIEF DESCRIPTION OF THE DRAWINGS

The invention description below refers to the accompanying drawings, of which.

DETAILED DESCRIPTION OF ILLUSTRATIVE EMBODIMENTS

Figure 1:
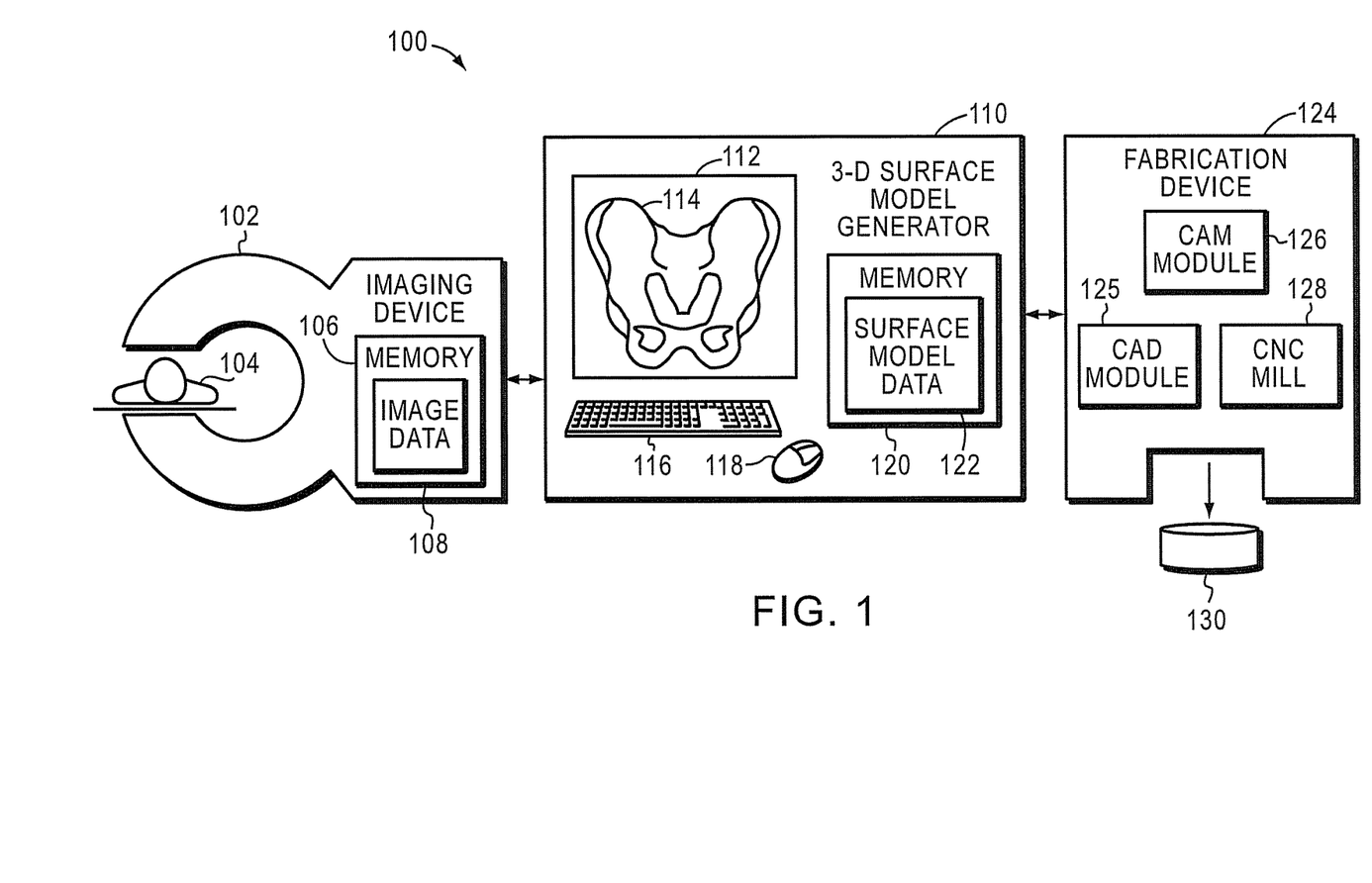
FIG. 1 is a schematic illustration of a system in accordance with an embodiment of the present invention.

FIG. 1 is a schematic illustration of a system 100 in accordance with an embodiment of the invention. The system 100 includes an imaging device 102, which may be positioned to take one or more images of a patient 104. The imaging device 102 may include a memory 106 for storing image data 108 taken of the patient 104. A 3-D surface model generator 110 is coupled to the imaging device 102, and receives the one or more images of the patient. That is, the 3-D surface model generator 110 may receive the image data 108 or a portion thereof. Alternatively or additionally, the 3-D surface model generator 110 may receive information derived from the one or more images or image data 108.

The 3-D surface model generator 110 is configured to generate a 3-D surface model based on the image data 108 received from the imaging device 102. In an embodiment, the 3-D surface model generator 110 includes a display 112, such as a CRT or flat screen display, for displaying a 3-D surface model 114 to a physician. As described herein, the 3-D surface model generator creates a surface model of that portion of the patient's anatomy, which is the subject of the surgical procedure. As understood by those skilled in the art, the surface model may be a mathematical model that represents the patient's anatomy. In the illustrated embodiment, the model 114 is of the patient's pelvis. The 3-D surface model generator 110 also may include one or more input devices, such as a keyboard 116 and a mouse 118, for receiving inputs from the physician. The 3-D surface model generator 110 also may include a memory 120 for storing surface model data 122.

A fabrication device 124 is coupled to the 3-D surface model generator and receives at least a portion of the 3-D model that represents the patient's anatomy. For example, the fabrication device 124 may receive some or all of the surface model data 122 produced by the 3-D surface model generator 110. The fabrication device 124 may include a computer aided design (CAD) module 125, a computer aided machine (CAM) module 126 and a computer numerical control (CNC) machine or mill. As described herein, the fabrication device 124 creates one or more templates, such as template 130, for use by the physician during a surgical procedure on the patient 104.

Each template created by the fabrication device 124 is custom made to fit the anatomy of a particular patient based on the surface model data 122 for that patient. In an embodiment, the template 130 is fabricated such that it may only be attached to or placed on the patient 104 in a single orientation relative to the patient. As described herein, the template 130 provides a visual guide, which the physician may use during the surgical procedure to affix a component to the patient's anatomy in a desired location and/or orientation relative to the patient's anatomy.

Suitable imaging devices 102 for use with the present invention include CT, PET, MRI and ultrasound, among others. The 3-D surface model generator 110 may be implemented on a personal computer or workstation, such as a laptop or notebook computer. The 3-D surface model generator 110 may include one or more units or modules, which may be implemented in software, hardware or a combination of both software and hardware, that are configured to produce the surface model from the image data 108, and to store the surface model data 122. Suitable 3-D surface model generators modules for use with the present invention include the 3D-Doctor modeling software from Able Software Corp. of Lexington, Mass. Suitable fabrication devices for use with the present invention in addition to CNC milling machines include rapid prototyping devices.

It should be understood that the imaging device 102, the 3-D surface model generator 110 and the fabrication device 124 may be interconnected by a communications network, such as the Internet or a private local area network (LAN). It should also be understood that, instead of interconnecting the imaging device 102, the 3-D surface model generator 110 and the fabrication device 124, data may be passed from one component to another using computer readable media, such as CDs, DVDs, or portable flash drives.

It should be understood that the system 100 of FIG. 1 is meant for illustrative purposes only and that various elements of the system may be combined in different ways. For example, the 3-D surface model generator 110 and fabrication device 124 may be combined into a single unit. Alternatively, the CAD module 125 may be included in the 3-D surface model generator. Those skilled in the art will understand that other such modifications may be made.

It should also be understood that the 3-D surface model generator need not display a model to the physician. For example, surface data may be provided directly to the fabrication device for fabrication of the template.

Figure 2A:
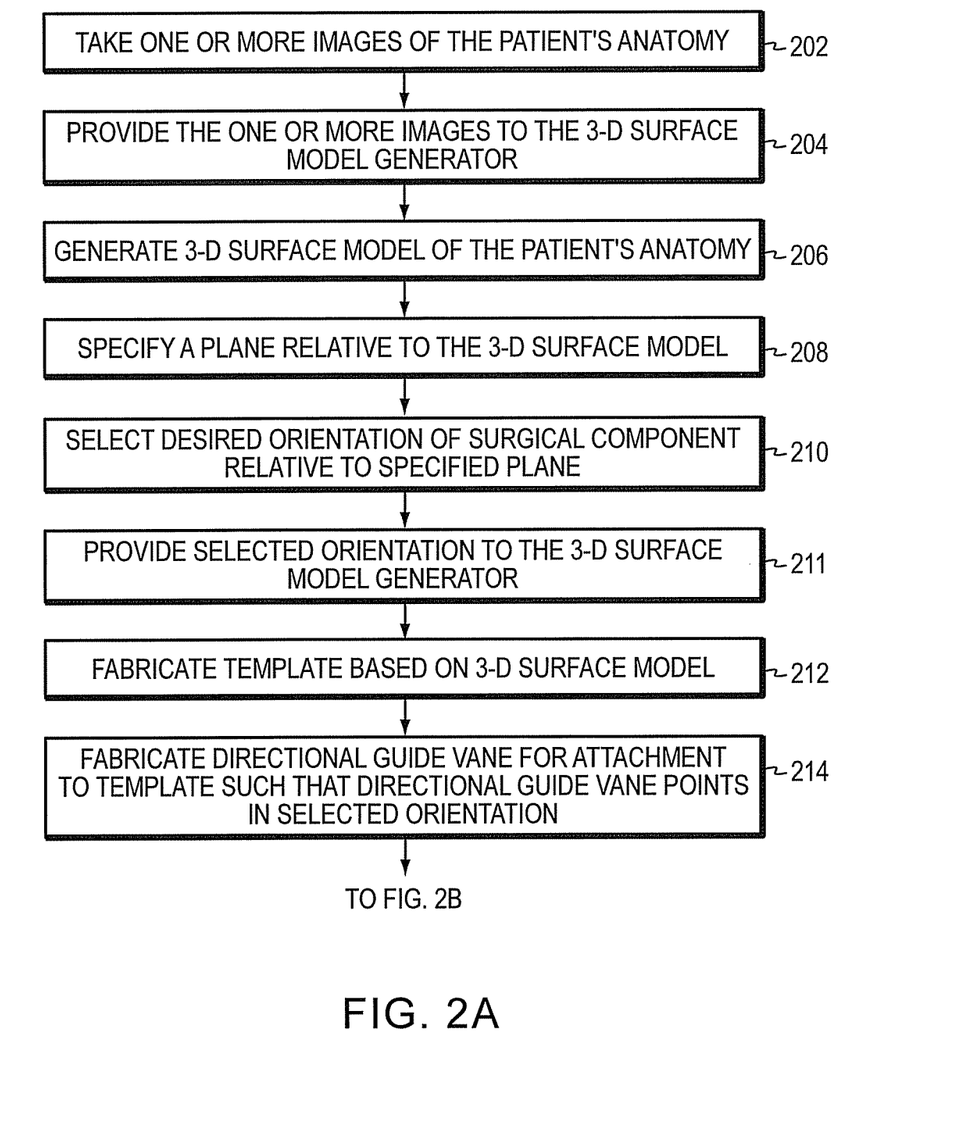
FIGS. 2A and 2B are a flow diagram of a method in accordance with an embodiment of the invention.
Figure 2B:
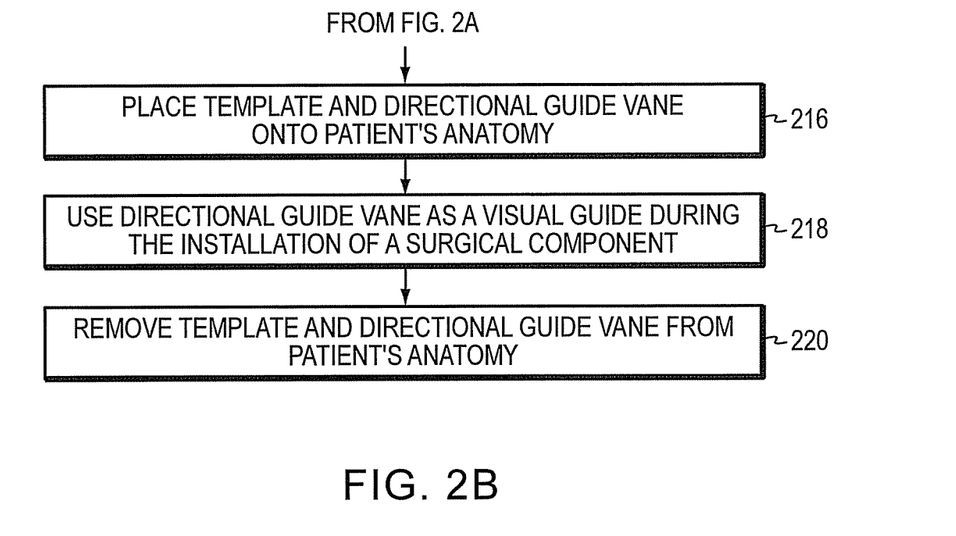

FIGS. 2A and 2B are a flow diagram of a method in accordance with an embodiment of the present invention. It should be understood that fewer or additional steps may be performed. One or more images are taken prior to the surgical procedure using the imaging device 102, as indicated at block 202 (FIG. 2A). In the illustrative embodiment in which the patient is undergoing total hip arthroplasty, the one or more images are taken of the patient's pelvis. The one or more images and/or image data 108 are passed from the imaging device 102, and received by the 3-D surface model generator 110, as indicated at block 204. The 3-D surface model generator 110 processes the received data and produces a 3-D surface model 114 of the patient's anatomy, as indicated at block 206. It should be understood that the 3-D surface model generator 110, in an alternative embodiment, additionally or alternatively may create a solid model of the patient's anatomy.

Figure 3:
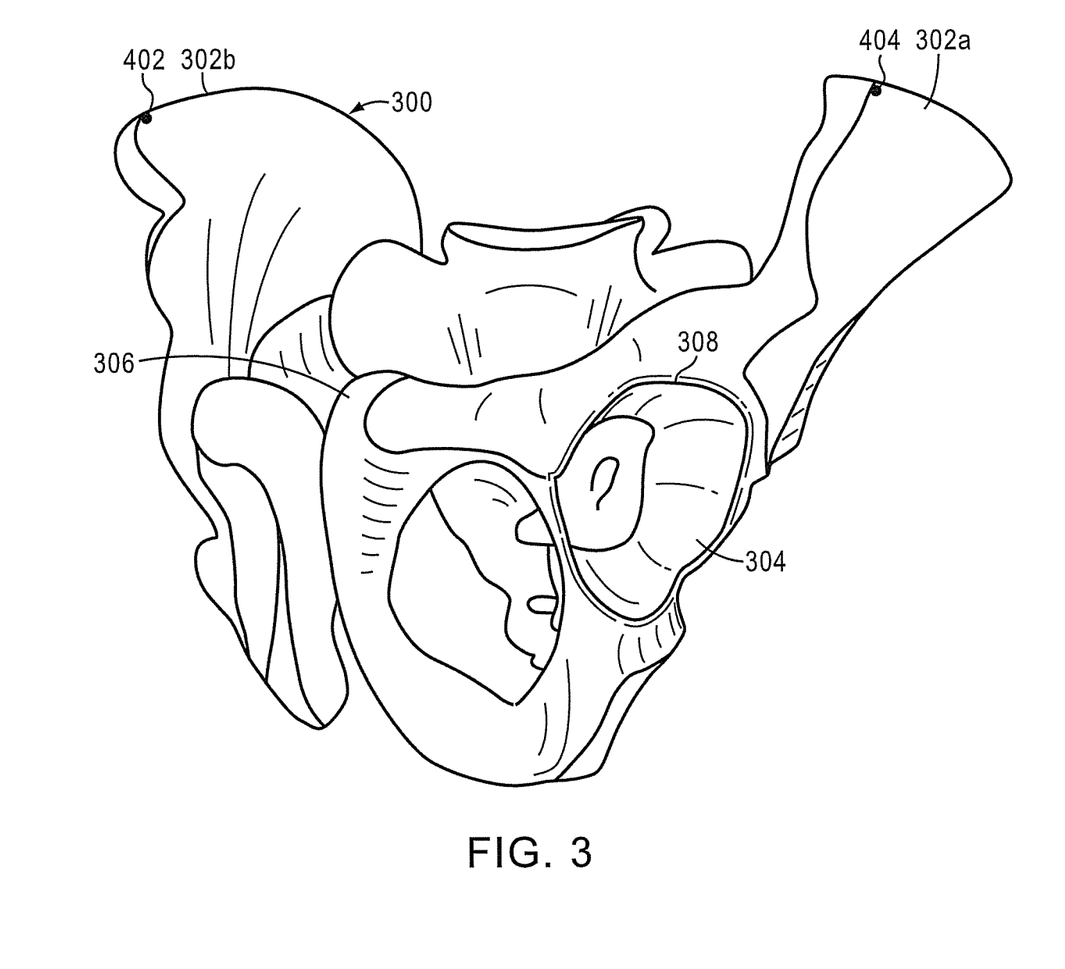
FIGS. 3 and 4 are views of a 3-dimensional surface model of a pelvis generated by the system of FIG. 1.

FIG. 3 is an illustration of a 3-D surface model of a pelvis 300 produced by the 3-D surface model generator 110 for display on display 112. The 3-D surface model 300 includes the various features of the patient's pelvis, such as the left and right iliac crests 302a, 302b, the left acetabulum 304, and the pubic symphisis 306. The acetabulum is a concave structure formed in the pelvis that receives the head of the femur. Surrounding the concave structure of the acetabulum is a generally circular rim 308. This rim 308 is uneven and roughly shaped, like the rim of a crater. That is, the rim rises and falls along its circumference, and the surface just outside of the rim 308 is similarly rough and uneven.

The resolution of the 3-D surface model 300 generated by the 3-D surface model generator 110 is sufficiently fine, i.e., detailed, to represent the rough surface of the interior of the acetabulum, the rough surface of the acetabular rim, and the rough surface of the area just outside of the rim.

In an embodiment, the physician may rotate the displayed 3-D surface model 300 about one or more axes to better examine the areas of interest, such as the acetabulum.

The physician may specify a plane relative to the pelvis, as indicated at block 208.

Figure 4:
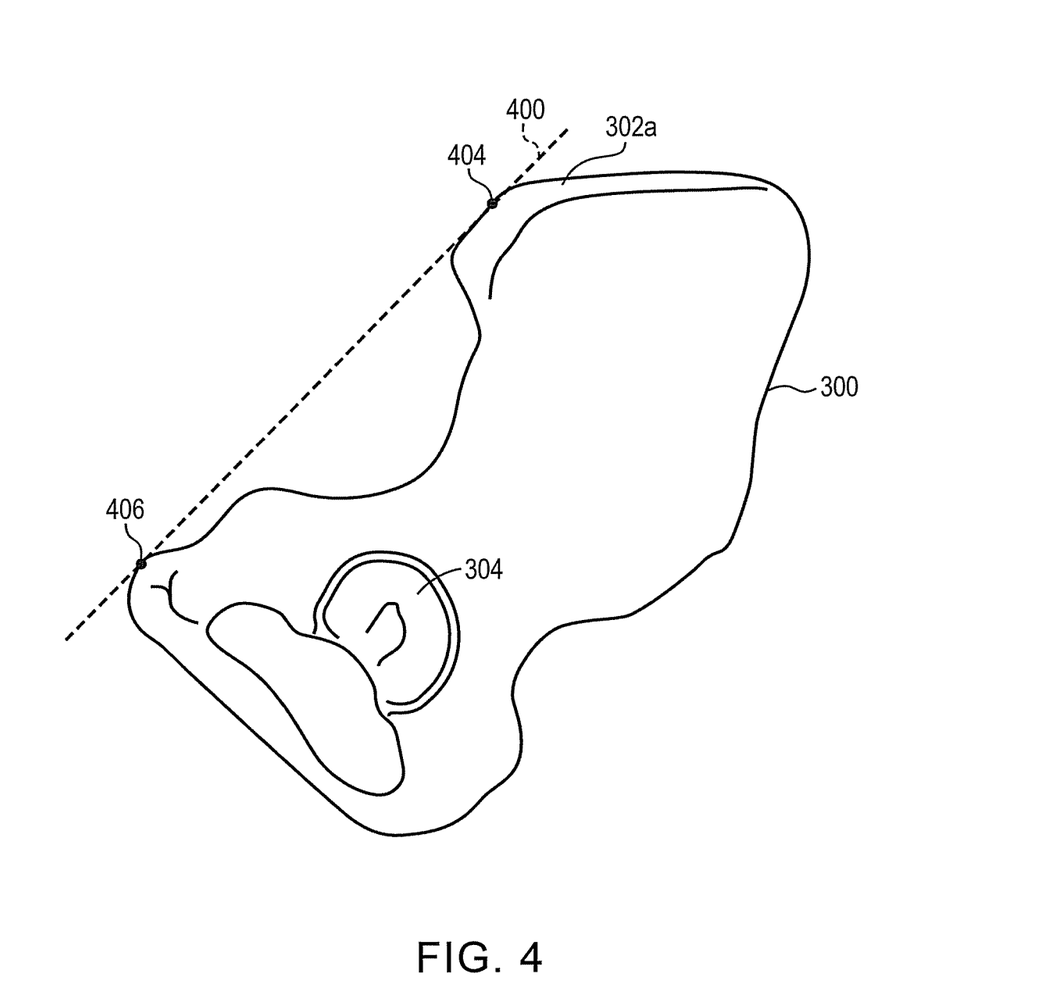

FIG. 4 is an illustration of the 3-D surface model of the pelvis 300 including a plane 400 as specified by the physician. To define the plane 400, the physician may select three points on the surface of the pelvis 300 using the mouse 118. For example, the physician may select a first point 402 on the right anterior superior iliac spine 302a, a second point 404 (FIG. 3) on the left anterior superior iliac spine 302b, and a third point 406 on the pubic symphysis 306, thereby defining an anterior pelvic (AP) plane 400. The 3-D surface model generator 110 may include a plane generator that is configured to generate a plane relative to the surface model 300 based on the three selected points 402, 404 and 406, and to display a representation of this plane, e.g., plane 400, on the display 112.

As indicated above, in performing hip arthroplasty, a prosthetic acetabular cup component is inserted into the patient's acetabulum. In addition, the head of the patient's femur is either removed and replaced with a prosthetic head that is received within the prosthetic acetabular cup component or the femoral head is resurfaced and received within the prosthetic acetabular cup component. The proper positioning of the acetabular cup component within the acetabulum affects the success of the operation. The orientation of the cup component may be defined in terms of abduction, which is rotation within the AP plane 400, and flexion, which is rotation normal to the AP plane and normal to the transaxial plane. Thus, the physician may select a desired abduction angle and a desired flexion angle for the acetabular cup component for a particular patient, such as 40 degrees abduction and 25 degrees flexion, as indicated at block 210. The physician may input these angles to the 3-D surface model generator 100, as indicated at block 211. The 3-D surface model generator 100 may be configured to present on the display 112 a Graphical User Interface (GUI) that has one or more fields for receiving such information, e.g., selected abduction and flexion angles, from the physician.

It should be understood that the physician may define the orientation of the cup component in other terms, such as abduction and anteversion, which is the angle in the transaxial (sometimes referred to as the transverse plane). It should also be understood that the 3-D surface model generator 110 may be configured to support all these means of defining the cup orientation as well as other such means, and that the physician may choose which terms to use, such as abduction and flexion, abduction and anteversion, etc.

The fabrication device 124 fabricates a template for placement on or attachment to the patient's acetabulum, as indicated at block 212. As described herein, the template includes a directional guide vane that, upon attachment of the template to the patient points in the direction selected by the physician relative to the AP plane 400. That is, with the template attached to the patient's anatomy, the guide vane is oriented relative to the AP plane 400 along the abduction and flexion angles selected by the physician. The directional guide vane and the template may be a single integral workpiece, or the guide vane may be removably attached to the template.

The CAD module 125 utilizes the known placement and shape of the template relative to the AP plane 400, the known geometry of the support, if any, used to attach the directional guide vane to the template, such as a mounting arm, and the selected orientation, e.g., abduction and flexion angles, to design the template and directional guide vane such that the guide vane intersects or points to the to the AP plane 400 in the selected direction, e.g., with the selected abduction and flexion angles, as indicated at block 214.

The template and directional guide vane may be fabricated from surgical grade materials, such as stainless steel, titanium alloy, etc.

It should be understood that blocks 204-214 correspond to steps performing during a pre-operative planning stage or phase of the surgical procedure. With the custom template fabricated, the physician may perform the surgical procedure.

Figure 5:
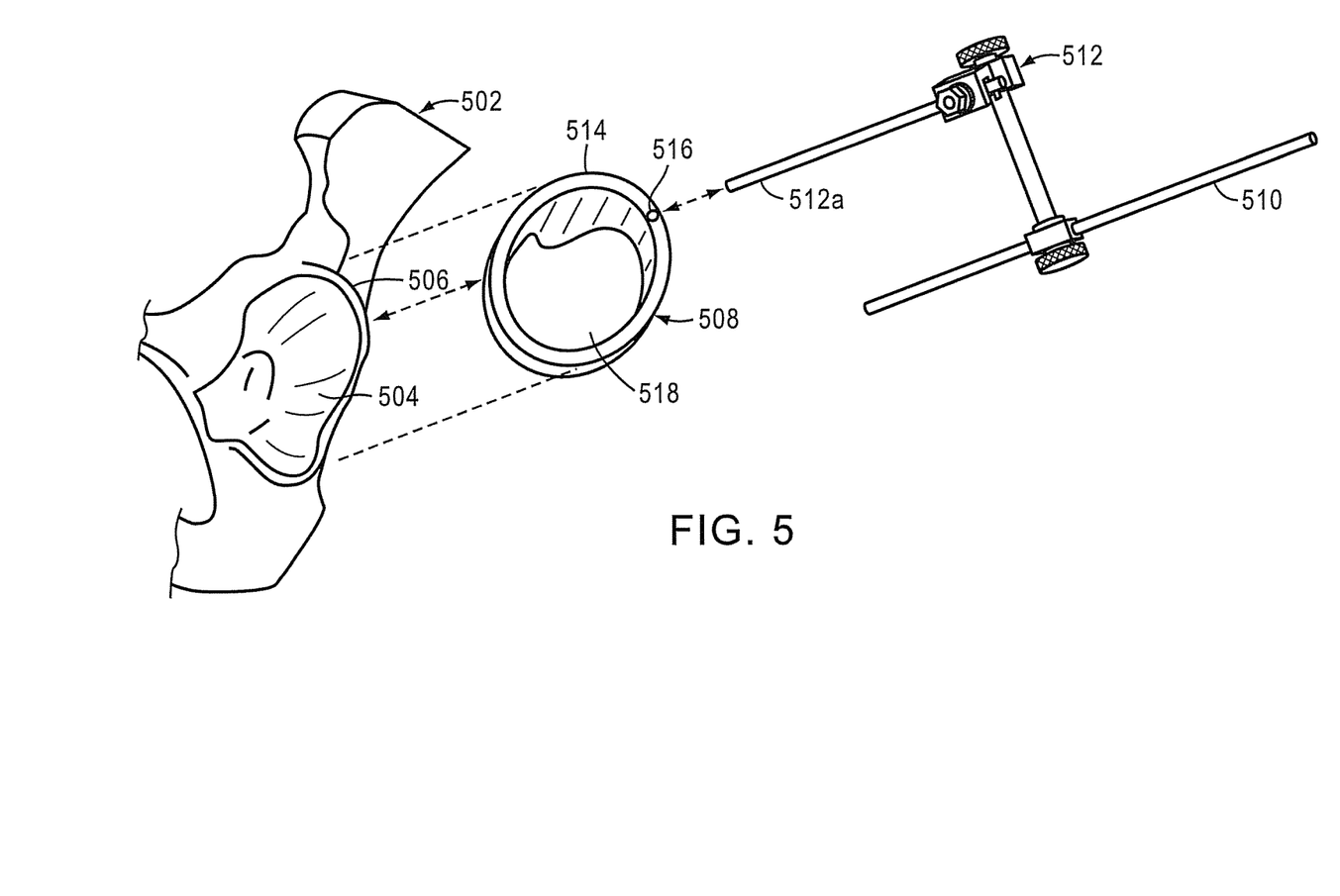
FIG. 5 is a side view of a pelvis including an exploded view of a template and directional guide vane according to an embodiment of the present invention.

FIG. 5 is a partial side view of the patient's pelvis 502 showing the patient's acetabulum 504 and acetabulum rim 506 with a custom fitted template 508 and a directional guide vane 510 shown in exploded view. In an embodiment, a mounting arm 512 attaches the directional guide vane 510 to the custom fitted template 508. The custom fitted template 508 may be generally circular shaped to mate with all or a substantial portion of the patient's acetabular rim 506. Because the template 508 matches the rough and uneven shape of the acetabular rim 506, it fits to the rim 506 and thus the pelvis in a single orientation. The template 508 may have an upper surface 514. Formed in the upper surface 514 may be a registration hole 516. The registration hole 516 is shaped to receive a lower portion 512a of the mounting arm 512. In an embodiment, the shape of the registration hole 516 and the lower portion 512a of the mounting arm 512 are selected so that there is only one way in which to attach the mounting arm 512 to the template 508. The template 508 may have an open interior 518 so that the template does not interfere with the placement of an acetabular cup component within the patient's acetabulum 504. Because the mounting arm 512 and guide vane 510 are rigidly attached to the template 508, the orientation of the guide vane 510 relative to the pelvis, and thus the AP plane 400, is known.

Figure 6:
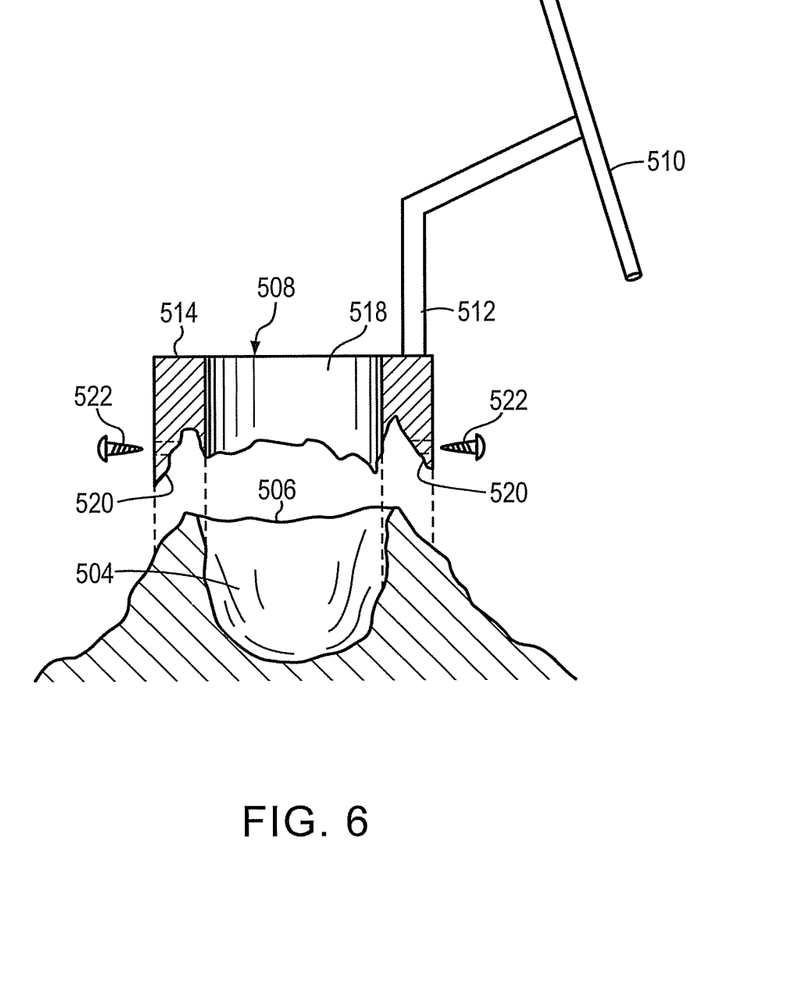
FIG. 6 is a cross-sectional side view of an acetabulum, template and directional guide vane according to an embodiment of the present invention.

FIG. 6 is a cross-sectional side view of the patient's acetabulum 504 with the custom template 508 about to be fitted around the acetabular rim 506. The template 508 has a lower surface 520 opposite the upper surface 514. The lower surface 520 is shaped by the fabrication device 124 so that it mates the acetabular rim 506. Furthermore, because the acetabular rim 506 as well as the area around the rim 506 is rough and uneven, the template 508 will only fit the acetabular rim 506 in a single orientation. The template 508 is placed in position on the acetuabular rim 506 by the physician, as indicated at block 216 (FIG. 2B). The template 508 may be held in place by one or more fasteners, such as screws 522.

Figure 7:
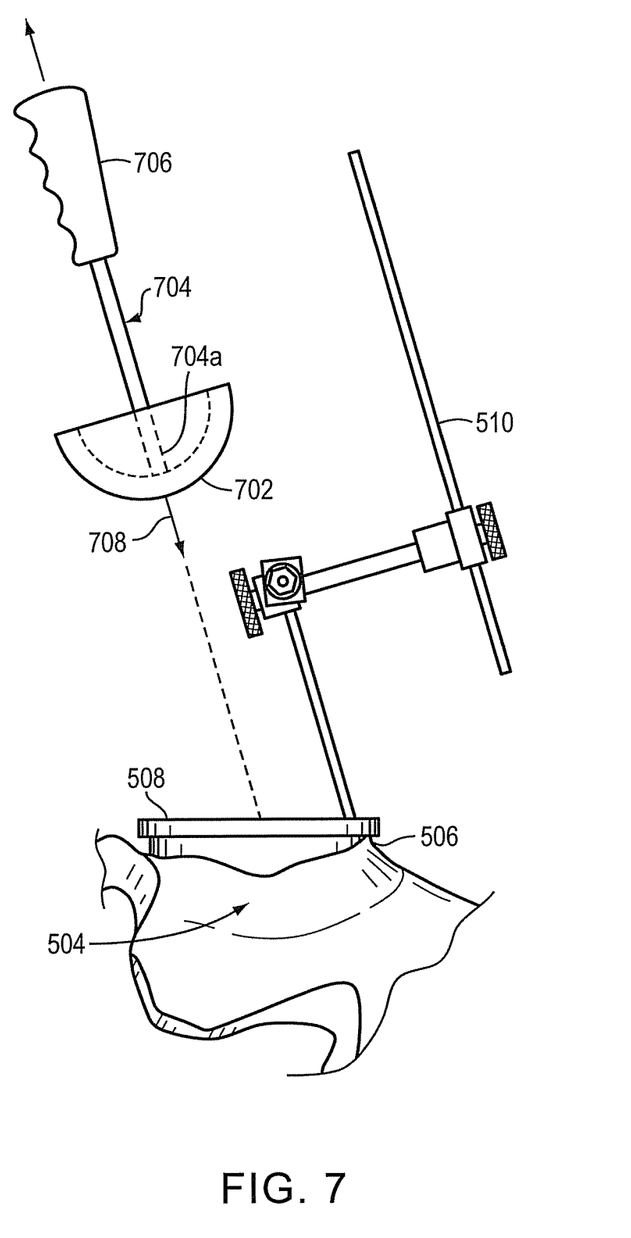
FIG. 7 is a side view of a template and directional guide vane attached to a patient's acetabulum.

FIG. 7 is a side view of the patient's acetabulum 504 with the template 508 attached around the acetabular rim 506. With the template 508 attached, and the directional guide vane 510 fixed in space relative to the patient's pelvis and thus the AP plane 400 (FIG. 4), the physician proceeds to place an acetabular cup component 702 within the acetabulum 504. The physician may use an insertion tool 704 having a handle 706 that may be grasped by the physician. Attached to an end of the insertion tool 704 opposite the handle 706 is the acetabular cup component 702. The physician uses the directional guide vane 510 as a visual guide or cue in placing the cup component 702 within the patient's acetabulum 504, as indicated at block 218.

In particular, the insertion tool 704 defines a major axis, indicated by arrow 708, along its length. In addition, the cup component 702 is removably attached to the insertion tool 704 such that the major axis 708 of the insertion tool 704 is co-axial with a central axis of the cup component 702. For example, the insertion tool 704 may have a threaded end 704a that engages a threaded portion of the cup component 702. Using the insertion tool 704, the physician may place the cup component 702 within the acetabulum 504 such that the major axis 708 of the insertion tool 704 is aligned with, i.e., parallel to, the directional guide vane 510. As the directional guide vane 510 is oriented along and thus points to the selected abduction and flexion angles relative to the AP plane 400 selected by the physician during the pre-operative planning phase, by visually aligning the major axis 708 of the insertion tool 704 with the directional guide vane 510, the cup component 702 (whose central axis is co-axial with the major axis 708 of the insertion tool 704) may be inserted in the desired orientation relative to the AP plane 400.

The physician may compare the orientation of the insertion tool 704 with the directional guide vane 510 from several vantage points to assure himself or herself that the insertion tool 704 and thus the cup component 702 is aligned with, i.e., parallel to, the directional guide vane 510. After the acetabular cup component 702 has been inserted, the template 508 and directional guide vane 510 may be removed and the surgical procedure completed, as indicated at block 220.

Because the template is custom made for each patient based on the particular shape of the rim of the patient's acetabulum, the template cannot be reused for other patients. The mounting arm 512 and directional guide vane 510, however, may be removed from the template, and re-used with templates formed for other patients.

It should be understood that various modifications may be made to the template and/or the directional guide vane without departing from the intent or scope of the invention. For example, the mounting arm 512 and/or guide vane 510 may be fixedly attached to the template, rather than be removable.

In another embodiment, a set of templates may be created based on statistical data generated from a population of patients regarding the size and shape of acetabulums. Each template in the set may be designed for a class of patients, such as male, female, over 60 years of age, etc. At least one of the templates from this set would fit most patients. In this embodiment, the 3-D surface model generator may be further configured to evaluate the patient's acetabulum and select the template from the set that provides the best fit. With this embodiment, the fabrication device may be eliminated.

Figure 8:
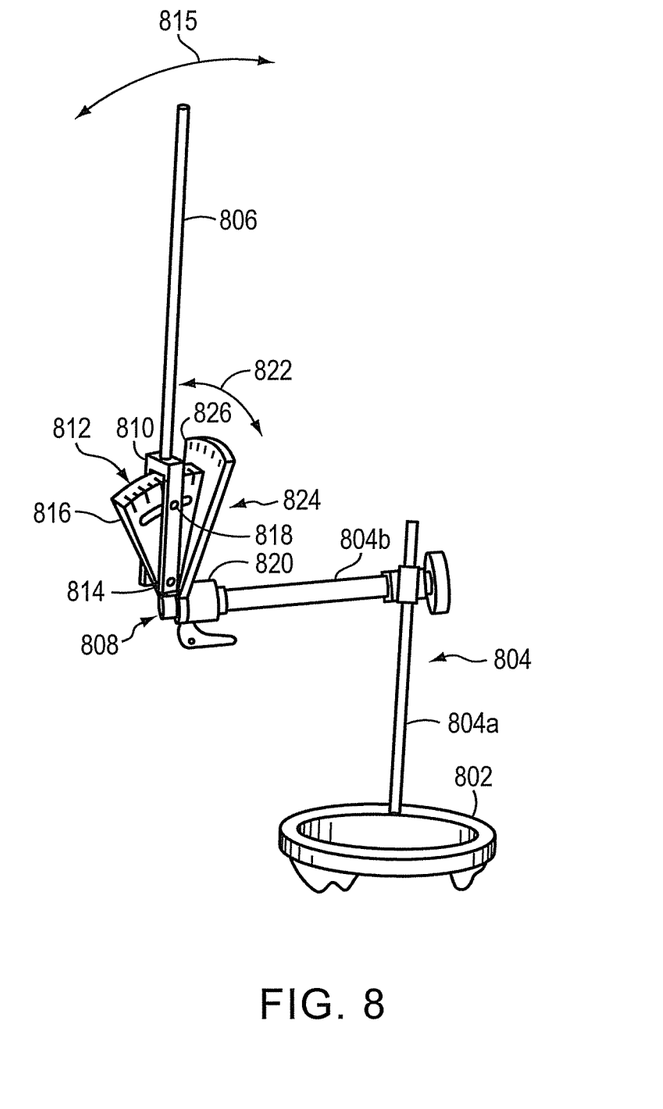
FIGS. 8-10 are side views of other embodiments of the present invention.

FIG. 8 is a side view of a template 802, mounting arm 804 and directional guide vane 806 according to another embodiment. In this embodiment, the directional guide vane 806 is rotatable within two planes relative to the pelvis. The mounting arm 804 may have a first leg 804a and a second leg 804b. The directional guide vane 806 is attached to the mounting arm 804 through a dual hinged hub 808. In an embodiment, the two hinges of the dual hinged hub 808 are oriented at ninety (90) degrees to each other. In particular, the guide vane 806 may be attached to a first hinged support 810, which may be pivotally attached to a first plate 812 by a pin 814, allowing the guide vane 806 to pivot within the first plane as indicated by arrow 815. The first plate 812 may have markings 816 formed thereon that provide a scale for indicating the angular orientation of the guide vane 806 within the first plane represented by the first plate 812. A releasable lock 818 holds the guide vane 806 in the selected position relative to the first plate 812.

The first plate 812 and thus the hinged support 810 and the guide vane 806 may be attached to the second leg 804b of the mounting arm 804 by a sleeve 820 such that the first plate 812, hinged support 810 and guide vane 806 pivot about the second leg 804b of the mounting arm 804 as an integral unit within the second plane, as indicated by arrow 822. A second plate 824 that is orthogonal to the first plate 812 may be fixed to the second leg 804b of the mounting arm 804. The first plate 812 may slide across the second plate 824 as the first plate 812 pivots about the second leg 804b of the mounting arm 804 through sleeve 820. A lock (not shown) may be used to fix the placement of the first plate 812 relative to the second plate 824. The second plate 824 also may have markings 826 formed thereon that provide a scale for indicating the angular orientation of the first plate 812 and thus the guide vane 806 relative the second plate 824.

In an embodiment, one of the plates, e.g., the first plate 812, is aligned with the AP plane 400 (FIG. 4), and the other plate, e.g., the second plate 824, is normal to the AP plane 400. With this embodiment, the directional guide vane 806 may be pivoted within the AP plane 400 for abduction, and normal to the AP plane 400 for flexion. In this way, the physician may "dial in" the desired angles using the scales 816 and 826 provided on the plates 812 and 824.

During surgery, the physician may select a desired abduction angle by adjusting the hinged support 810 relative to the first plate 812, and may select a desired flexion angle by adjusting the first plate 812 relative to the second plate 824. These angles may be adjusted based on factors arising during the surgical procedure.

In an alternative embodiment, the directional guide vane 806 may be adjustable about a single axis, e.g., within or normal to the AP plane 400.

Figure 9:
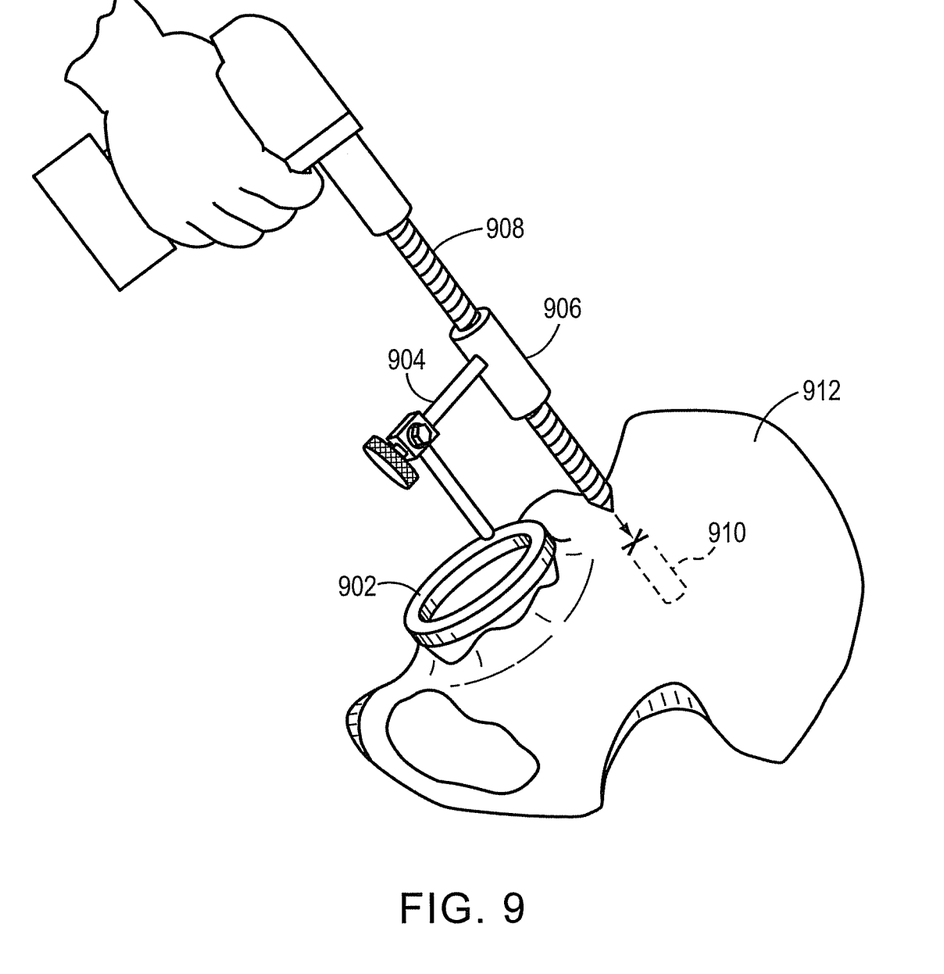

FIG. 9 is a side view of another embodiment of the present invention. In this embodiment, a drill guide is attached to the template rather than the guide vane. Specifically, a custom template 902 is formed by the fabrication device 124 (FIG. 1). A mounting arm 904 is attached to the custom template 902. Attached to the mounting arm 904 is a drill guide 906. The drill guide 906 is mounted to the template 902 such that, when a drill bit 908 is placed within the guide 906, the drill bit 908 is in the orientation relative to the AP plane 400 (FIG. 4) selected by the physician. During the surgical procedure, the physician uses the drill guide 906 to drill a pilot hole 910 into the patient's pelvis 912.

Figure 10:
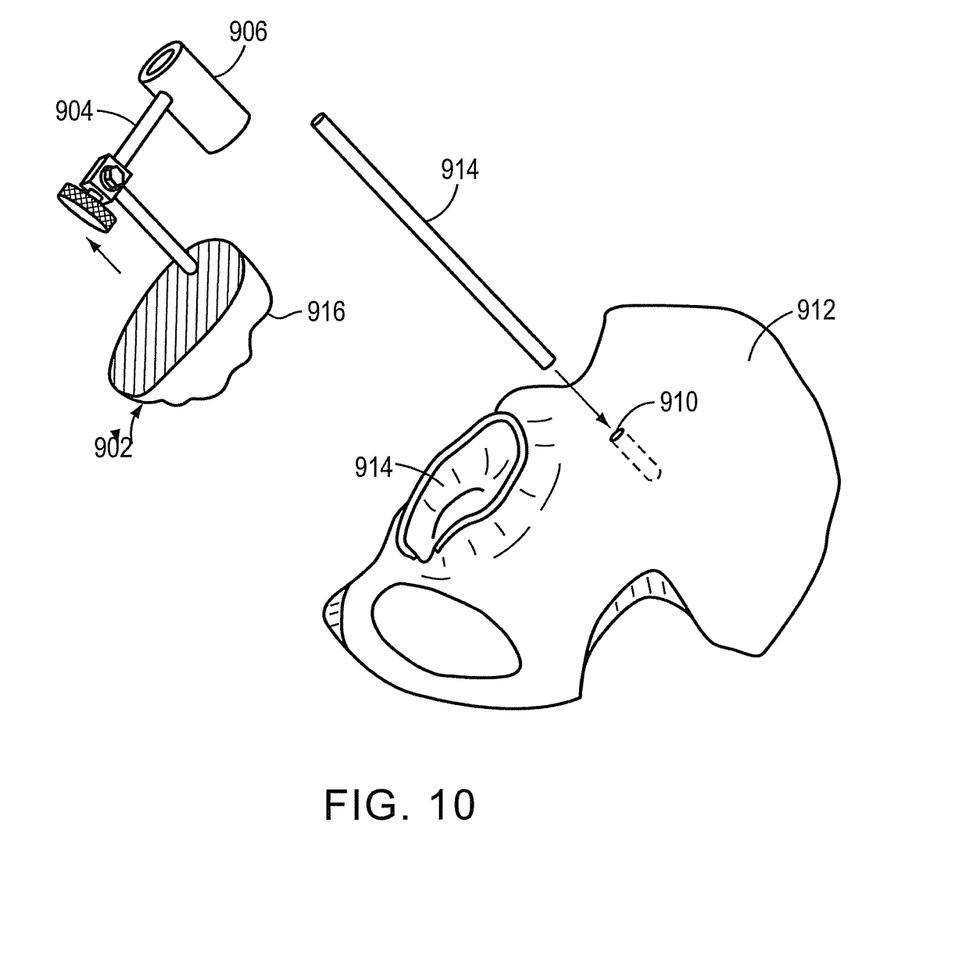

Referring to FIG. 10, the template 902 and drill guide 906 may be removed from the patient's pelvis 912. A directional guide vane 914 may be placed in the pilot hole 910. Because the pilot hole 910 was formed in the selected orientation relative to the AP plane 400, the directional guide vane 914, which extends out from the pilot hole 910, is also oriented along the selected direction relative to the AP plane 400. The physician may use the directional guide vane 914 as a visual guide or cue to place the component in the desired orientation as described above. The directional guide vane 914 may be cylindrically shaped to fit snugly within the pilot hole 910.

In another embodiment, a short pin (not shown) may be placed in the pilot hole such that a portion of the pin extends above the pelvis. The directional guide vane may have a hollow end configured to fit around the portion of the pin extending above the pelvis.

In this embodiment, the template 902 may be semispherically shaped to sit within the patient's acetabulum 914. That is, the template 902 may have a lower surface 916 shaped to mate with the concave interior surface of the acetabulum 914.

A further variation in the use of the template involves its combination with computer-assisted surgical navigation using optical, electromagnetic, or other means of tracking. In any of these processes, a coordinate system for the pelvis must be defined. This coordinate system may be the anterior pelvic (AP) plane or another plane. Since the mathematical relationship between the template and the AP plane 400, may be determined preoperatively by the 3-D surface model generator 110 and/or the CAD module 125, placement of the template onto the patient's acetabulum and then measurement of its location using a navigation system can be used to rapidly determine the orientation of the pelvis. The template can then be removed and surgical navigation can proceed as usual thereafter.

The foregoing has been a detailed description of illustrative embodiments of the invention. Various modifications and additions can be made without departing from the spirit and scope thereof. Accordingly, this description is meant to be taken only by way of example, and not to otherwise limit the scope of the invention.

What is claimed is:

1. A method comprising:
   accessing image data of at least a portion of a pelvis of a patient, the at least a portion of the pelvis including an acetabulum, the acetabulum having an outer surface;
   creating a computer-based surface model of the at least a portion of the pelvis including the outer surface of the acetabulum from the image data;
   defining a coordinate plane for the computer-based surface model;
   determining an orientation of a prosthetic acetabular cup component relative to the coordinate plane;
   utilizing the computer-based surface model to generate manufacturing data for fabricating a template that includes a first surface shaped to mate with the outer surface of the acetabulum in a single orientation;
   fabricating the template based on the manufacturing data, wherein the template fits to the acetabulum of the patient in the single orientation, and
   attaching a directional guide to the template, wherein the directional guide provides a visual indication of the orientation of the prosthetic cup component when the template is fitted to the acetabulum in the single orientation.

2. The method of claim 1 further comprising:
   generating the image data utilizing at least one of computerized tomography (CT) scanning, positron emission tomography (PET) scanning, magnetic resonance imaging (MRI), or ultrasound imaging.

3. The method of claim 1 wherein the coordinate plane is an anterior pelvic (AP) plane.

4. The method of claim 1 wherein the orientation of the prosthetic acetabular cup component is defined in terms of abduction and flexion.

5. The method of claim 1 wherein the computer-based surface model is three-dimensional (3D).

6. A method comprising:
   providing a template with a first surface shaped to mate with an outer surface of an acetabulum of a pelvis of a patient, where the first surface is configured such that the template fits to the acetabulum in a single orientation;
   placing the template at the acetabulum of the patient in the single orientation, where the template, when placed at the acetabulum has a location and establishes a mathematical relationship with a coordinate system defined for the pelvis of the patient;
   determining, by a surgical navigation system, the location of the template as placed at the acetabulum; and
   utilizing the location of the template as determined by the surgical navigation system and the mathematical relationship between the template and the coordinate system to implant a prosthetic component at the acetabulum of the patient at a desired orientation.

7. The method of claim 6 further comprising:
   determining the mathematical relationship between the template and the coordinate system preoperatively to a surgical procedure on the pelvis of the patient.

8. The method of claim 7 wherein the determining the mathematical relationship between the template and the coordinate system is performed by a three dimensional (3D) surface model generator or a Computer Aided Design (CAD) system.

9. The method of claim 6 wherein the coordinate system defined for the pelvis is an anterior-pelvic (AP) plane coordinate system.

10. The method of claim 9 further comprising:
    indicating, by the surgical navigation system, a direction relative to the AP plane coordinate system.

11. The method of claim 10 wherein the prosthetic component is an acetabular cup component and the direction indicates the desired orientation for implanting the acetabular cup component at the acetabulum of the patient.

12. The method of claim 11 wherein the direction is defined by a selected abduction angle and a selected anteversion angle relative to the AP plane coordinate system.

13. The method of claim 6 wherein the surgical navigation system uses optical or electromagnetic tracking to determine the location of the template as placed at the acetabulum.

14. The method of claim 6 wherein the template is custom fabricated for the patient.

15. The method of claim 6 wherein the utilizing includes determining an orientation of the pelvis of the patient.

* * * * *